US00PP09455P

United States Patent [19]

Polys

[11] Patent Number: Plant 9,455

[45] Date of Patent: Feb. 20, 1996

[54] CHRYSANTHEMUM PLANT NAMED YELLOW BLUSH

[75] Inventor: Susan M. Polys, Salinas, Calif.

[73] Assignee: Yoder Brothers, Inc., Barberton, Ohio

[21] Appl. No.: 331,862

[22] Filed: Nov. 1, 1994

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS

P.P. 7,985 9/1992 VandenBerg ..... Plt./82.4
4,616,099 10/1986 Sparkes ..... 47/58

OTHER PUBLICATIONS

Broertjes, et al., 1980, "A mutant of a mutant of a . . . Irradiation of progressive radiation–induced mutants in a mutation breeding programme with *C. morifolium*", Euphytica, 29:525–530.

Gosling, ed., 1979, "The Chrysanthemum Manual–6th edition", The National Chrysanthemum Society, London, Essex Telegraph Press, Ltd., London, pp.329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the year Round", Blanford Press, London, pp. 27–29, 320–327.

*Primary Examiner*—Howard J. Locker
*Attorney, Agent, or Firm*—Foley & Lardner

[57] ABSTRACT

A Chrysanthemum plant named Yellow Blush particularly characterized by its flat capitulum form; daisy capitulum type; yellow ray floret color; diameter across face of capitulum of 127 to 140 mm when fully opened, when grown as a pinched disbudded pot mum; photoperiodic flowering response to short days of 53 to 58 days; plant height, with 20 to 22 long days after sticking unrooted cuttings and with 1 to 2 applications of 2500 ppm B-9 SP, ranges from 23 to 28 cm when grown as a pinched pot mum with 4 cuttings in a 15 cm pot; branching pattern is semi-spreading, each plant having 3 to 5 laterals after pinch; and recommended as disbudded pot mum.

1 Drawing Sheet

The present invention comprises a new and distinct cultivar of Chrysanthemum, botanically known as *Dendranthema grandiflora,* and referred to by the cultivar name Yellow Blush.

Yellow Blush, identified as 4801 (86-627M02), is a product of a mutation induction program. The new cultivar was discovered and selected by Susan M. Polys on Nov. 25, 1992 in a controlled environment in Salinas, Calif., as one flowering plant within a flowering block established as rooted cuttings from stock plants which had been exposed as unrooted cuttings to an X-ray source of 2000 rads in Fort Myers, Fla., on May 28, 1992. The irradiated parent cultivar was the cultivar identified as White Blush, disclosed in pending application Ser. No. 08/296,467, and described as a disbud daisy pot mum with a flat capitulum form; white ray floret color with a cream-white color of the immature ray florets; diameter across face of capitulum of 114 to 121 mm when fully opened, when grown as a pinched disbudded pot mum; flowering response period of 49 to 55 days after start of short days; plant height, with 20 to 22 long days after sticking unrooted cuttings and with 1 to 2 applications of 2500 ppm B-9 SP, of 20 to 30 cm when grown as a pinched pot mum in a 15 cm pot; semi-spreading branching pattern, with 3 to 5 laterals after pinch; and recommended as a disbudded pot mum.

The irradiation program resulting in Yellow Blush has as its primary objective the expansion of color ranges of the parent cultivar White Blush. The irradiation program comprised irradiating cuttings of the parent cultivar at irradiation levels of 1500, 1750 and 2000 rads. A total of 1402 cuttings harvested from a total of 225 irradiated plants were planted on Sep. 21, 1992. Of these, 5 initial selections were made, which selections were then revegetated and reflowered. Three consecutive flowerings resulted in discarding 3 of the original 5 selections on Aug. 3, 1993. Continued flowering trails resulted in the decision to introduce 1 of the remaining selection as Yellow Blush. One remaining selection is still maintained in our program as a possible future introduction.

The first act of asexual reproduction of Yellow Blush was accomplished when vegetative cuttings were taken from the initial selection in January 1993 in a controlled environment in Salinas, Calif., by technicians working under supervision of Susan M. Polys.

Horticultural examination of controlled flowerings of successive plantings has shown that the unique combination of characteristics as herein disclosed for Yellow Blush are firmly fixed and are retained through successive generations of asexual reproduction.

Yellow Blush has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Yellow Blush, which, in combination, distinguish this Chrysanthemum as a new and distinct cultivar:

1. Flat capitulum form.
2. Daisy capitulum type.
3. Yellow ray floret color.
4. Diameter across face of capitulum of 127 to 140 mm when fully opened, when grown as a pinched disbudded pot mum.
5. Photoperiodic flowering response to short days of 53 to 58 days.
6. Plant height, with 20 to 22 long days after sticking unrooted cuttings and with 1 to 2 applications of 2500 ppm B-9 SP, ranges from 23 to 28 cm when grown as a pinched pot mum with 4 cuttings in a 15 cm pot.
7. Branching pattern is semi-spreading, each plant having 3 to 5 laterals after pinch.

8. Recommended as disbudded pot mum.

The accompanying photographic drawing is a side view of a potted mum of Yellow Blush, with 4 cuttings in a 15 cm pot, with the colors being as nearly true as possible with illustrations of this type.

Of the commercial cultivars known to the inventor, the most similar in comparison to Yellow Blush is the parent cultivar White Blush. All traits of Yellow Blush are similar to those of White Blush, except for the ray floret color and the flowering response to short days. The ray floret color of Yellow Blush is yellow, while the ray floret color of White Blush is white, with a cream-white color of the immature ray floret. Flowering response to short days of Yellow Blush has been 2 to 4 days slower than the flowering response of White Blush.

In the following description color references are made to The Royal Horticultural Society Colour Chart. The color values were determined on plant material grown as a pinched spray pot mum in Salinas, Calif. on Mar. 8, 1994.

Classification:

*Botanical.*—*Dendranthema grandiflora* cv Yellow Blush.

*Commercial.*—Flat daisy disbud pot mum.

INFLORESCENCE

A. Capitulum:

*Form.*—Flat.

*Type.*—Daisy.

*Diameter across face.*—127 to 140 mm when fully opened.

B. Corolla of ray florets:

*Color (general tonality from a distance of three meters).*—Yellow.

*Color (upper surface).*—9A.

*Color (under surface).*—9C.

*Shape.*—Straight, pointed, slightly ribbed.

C. Corolla of disc florets:

*Color (mature).*—7B.

*Color (immature).*—144A to 144B.

D. Reproductive Organs:

*Androecium.*—Present on disc florets only; scant pollen.

*Gynoecium.*—Present on both ray and disc florets.

PLANT

A. General appearance:

*Height.*—23 to 28 cm when grown as a pinched pot mum with 20 to 22 long days prior to start of short days, and with 1 to 2 applications of 2500 ppm B-9 SP.

*Branching pattern.*—Semi-spreading, with 3 to 5 laterals after pinch.

B. Foliage:

*Color (upper surface).*—147A.

*Color (under surface).*—147B.

*Shape.*—Deeply lobed and slightly serrated.

I claim:

1. A new and distinct Chrysanthemum plant named Yellow Blush, as described and illustrated.

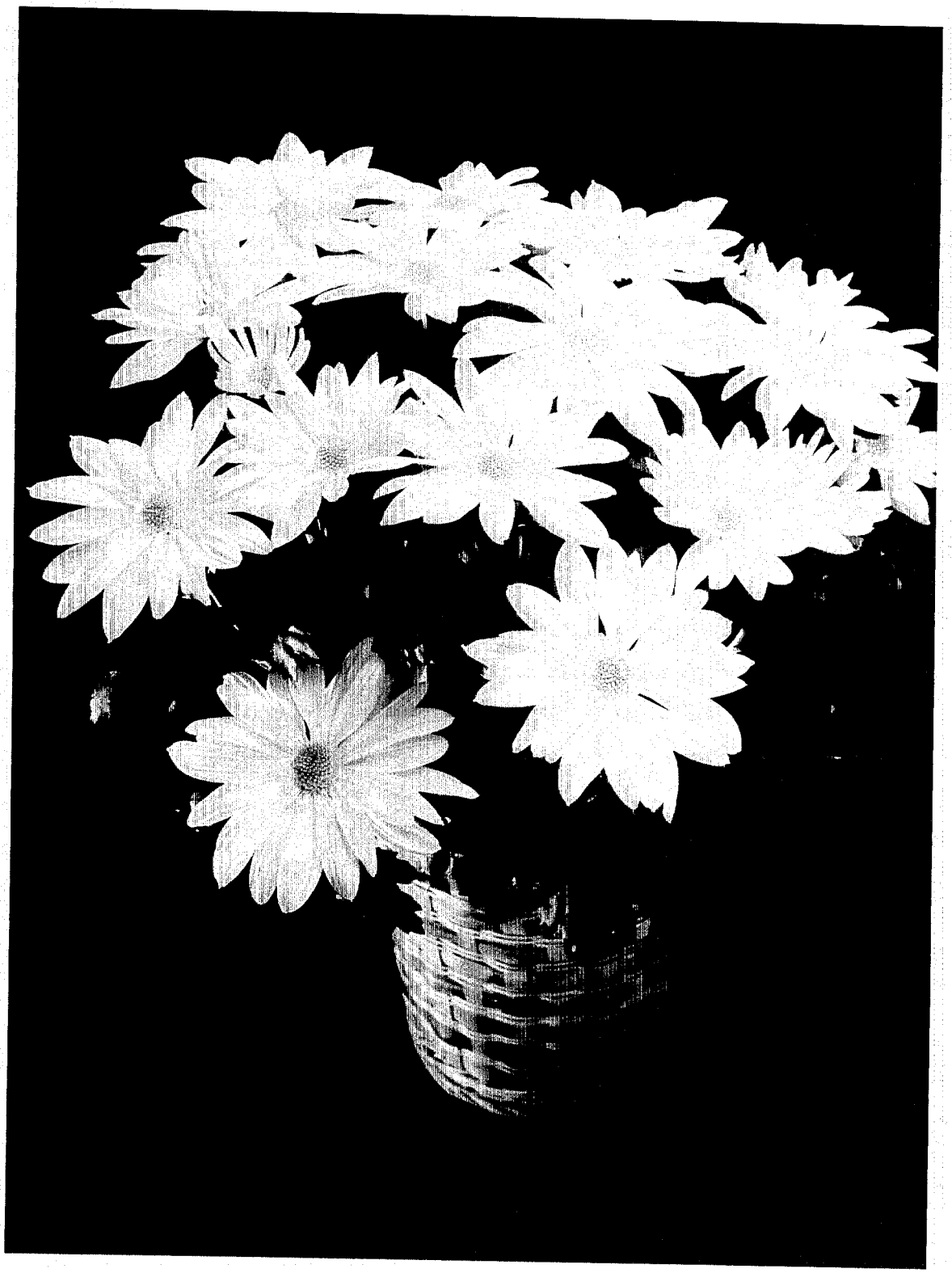

* * * * *